(12) United States Patent  (10) Patent No.: US 8,900,121 B2
Moon  (45) Date of Patent: Dec. 2, 2014

(54) CORRECTION APPARATUS FOR MALE PENIS

(76) Inventor: Heung-Sik Moon, Busan (KR)

(*) Notice: Subject to any disclaimer, the term of this patent is extended or adjusted under 35 U.S.C. 154(b) by 595 days.

(21) Appl. No.: 13/127,463

(22) PCT Filed: Sep. 9, 2009

(86) PCT No.: PCT/KR2009/005113
§ 371 (c)(1),
(2), (4) Date: May 3, 2011

(87) PCT Pub. No.: WO2010/053255
PCT Pub. Date: May 14, 2010

(65) Prior Publication Data
US 2011/0213201 A1 Sep. 1, 2011

(30) Foreign Application Priority Data
Nov. 6, 2008 (KR) .................. 10-2008-0110083

(51) Int. Cl.
A61F 5/00 (2006.01)
A61F 5/41 (2006.01)

(52) U.S. Cl.
CPC ............ *A61F 5/41* (2013.01); *A61F 2005/411* (2013.01); *A61F 2005/412* (2013.01); *A61F 2005/414* (2013.01)
USPC .......................................................... 600/39

(58) Field of Classification Search
USPC ................................................ 600/38–41
See application file for complete search history.

(56) References Cited

U.S. PATENT DOCUMENTS

| 5,707,341 | A | 1/1998 | Mathewuse | |
|---|---|---|---|---|
| 8,187,165 | B2* | 5/2012 | Park | 600/41 |
| 2005/0124854 | A1 | 6/2005 | Suchy et al. | |
| 2007/0093687 | A1 | 4/2007 | Hoefer | |
| 2010/0016656 | A1* | 1/2010 | Rudi | 600/39 |

OTHER PUBLICATIONS

International Search Report of PCT/KR2009/005113 dated on May 13, 2010.

* cited by examiner

*Primary Examiner* — John Lacyk
(74) *Attorney, Agent, or Firm* — Justin H. Kim; Maxon IP, LLC

(57) ABSTRACT

The present invention deals with a correction apparatus for a male penis and more specifically with a correction apparatus for a male penis, that enables the prevention and treatment of deviation whereby tissue stretching and bending correction and stimuli to sensitive areas has resulted in abnormal shapes including warped or bent shapes, impotence related to sexual function, glans enlargement, premature ejaculation and other sexual dysfunctions, and prostatitis.

14 Claims, 14 Drawing Sheets

CORRECTION APPARATUS FOR MALE PENIS

TECHNICAL FIELD

The present invention relates generally to fraction apparatuses for penises and, more particularly, to a traction apparatus for penises which can increase the size of a penis, correct a bent penis, and dull the sensitivity of the glans of a penis to treat premature ejaculation.

BACKGROUND ART

Penises are the genital organs of the males and cylindrical erective organs with portions of urinal ducts. The penises comprise a pair of corpus cavernosums and a corpus spongiosum and have a glans on the distal end thereof.

Such a penis is inflated by expansion of the corpus cavernosums to make sexuality possible when a large amount of blood is drawn into the penis by psychological or physical stimulation. If there is a sexual dysfunction, for example, impotence, where the penis cannot become erect despite normal psychological or physical stimulation, urological internal medicine or surgery is typically recommended to recover the sexual function.

Furthermore, in terms of shape, a penis preferably is straight in the longitudinal direction thereof but there may be penis plastica in which the penis is excessively curved or bent to one side. In this case, rather than a surgical operation, a separate device for correcting the shape of the penis is required. However, such a device has to date not been introduced on the market.

Meanwhile, microgenitalism where a penis is very small causes psychological inferiority and may make normal sexuality difficult. Thus, a lot of men use aids or undergo surgical operations to increase the penis size.

A traction apparatus for treating penis plastica was proposed in U.S. Pat. No. 7,276,040 (registered on Oct. 2, 2007). In this conventional apparatus, to support a penis at a fixed angle, support members are respectively fitted over a distal end and a proximal end of the penis, and the distance between the support members is extended and retained. However, this apparatus is only to correct a bent penis rather than providing effects to overcome microgenitalism or premature ejaculation.

Furthermore, in the foregoing conventional traction apparatus, each of extension units for extending the distance between the support members is formed by a combination of a plurality of components. However, there is a high probability of a loss of a component. Even if only one of the components is lost, the entire traction apparatus cannot be used. Therefore, it is difficult to store and maintain the extension unit. Moreover, to adjust the extension unit, the components of the extension unit which are disposed on opposite sides of the apparatus must be separately manipulated. This inconveniences the user.

An apparatus for correcting a bent penis to make a urinal duct straight to remove pain during urination was proposed in Germany Patent No. DE166188. However, this apparatus is only characterized in that it can correctly support the penis in response to the size and length of the penis, but it has no any function to overcome microgenitalism. In addition, this apparatus is only to treat penis plastica which causes pain during urination, but it does not have a structure for coping with different states of the penis after and before erection. Therefore, this apparatus is useless for treating microgenitalism or premature ejaculation, except for treating penis plastica.

Thus, to treat microgenitalism or premature ejaculation, separate surgical treatment or a separate apparatus is required. This is financially burdensome to the user.

Meanwhile, the conventional techniques have a glans receiving member which holds the glans of the penis so that the glans is supported by the extension units. However, the glans receiving member is brought into contact with the periphery of the glans and the contact area is comparatively large. Therefore, the periphery of the glans may be injured during the use of the apparatus.

Furthermore, the conventional techniques are inconvenient in that the two extension units, the glans receiving member which are supported by the extension units, and a base member which supports the extension units must always be used together. Although the user puts on all the components, the position and orientation of the penis is not maintained constant. Thus, it is inconvenient for the user to wear the apparatus in his daily routine.

In addition, the conventional traction apparatus includes an elliptical base member which supports proximal ends of the extension units and is disposed around the proximal end of the penis. After the penis has been inserted into the base member, the base member supports the proximal end of the penis. Here, because the base member surrounds the skin of the proximal end of the penis, a portion of the base member is disposed between the penis and testicles. Therefore, when the user who has put on the traction apparatus in a stand is sitting down, the elliptical base member into which the penis is inserted comes into contact with the testicles and presses them, thus causing pain. If the testicles enter the base member, it is inconvenient for the user to stand up and sit down.

Moreover, if the glans is comparatively small, it may be easily removed from the apparatus, thus making it difficult for the apparatus to hold the glans. However, to treat microgenitalism or penis plastica or to extend the penis, the apparatus must continuously be able to hold the penis over a predetermined period of time. However, in the conventional techniques, because it is difficult to reliably hold the entire glans, if the glans is comparatively small, it is undesirably easily removed from the apparatus. Furthermore, a frequent friction between the upper portion of the glans and the apparatus may cause an inflammation on the glans. In addition, because the base member is fixed with respect to the penis, it is very difficult for the user wearing the apparatus to exercise.

As such, the conventional techniques are effective only for treating penis plastica or extending the penis but are not effective for treating premature ejaculation, improving the erectility of the penis or extending the size of the glans. To improve these unsatisfactory points, separate medical prescription or a separate medical aid is required.

DISCLOSURE

Technical Problem

Accordingly, the present invention has been made keeping in mind the above problems occurring in the prior art, and an object of the present invention is to provide a traction apparatus for a penis which is configured in such a way that the traction structure to correct the shape of the penis and to extend the size thereof is simplified, thus facilitating maintenance, and reducing a probability of loss of components, and in which the length of the apparatus can be adjusted after the user has worn the apparatus, and even if the penis is pulled by excessive traction force or the fraction thereof is loosened, the existing state is maintained.

Another object of the present invention is to provide a traction apparatus for a penis in which a decompression unit for receiving the glans of the penis and creating a vacuum therein is supported by a wearing unit that is put on the user, and because the vacuum is created in the decompression unit and an opening of the decompression unit has an elastic stepped structure so that the glans of the penis is prevented from being undesirably removed from the decompression unit.

A further object of the present invention is to provide a traction apparatus for a penis which continuously applies traction force to the penis so that the penis shaft is tensioned, and extends the glans of the penis under the vacuum conditions, so that penis plastica and premature ejaculation can be treated and the penis can be extended in length and size, and the extension and decompression stimulate blood vessels, nerves and tissues of the penis, thus promoting blood circulation, thereby enhancing the erectility of the penis.

Yet another object of the present invention is to provide a traction apparatus for a penis which includes the wearing unit that is put on a portion of the user's body and holds the glans, a decompression body that receives the glans of the penis, and a longitudinal support member that supports the decompression body, and which allows the user to selectively use a combination among the above three elements; for example, a combination of the wearing unit and the decompression body, a combination of the decompression body and the longitudinal support member, or a combination of all three elements, so that the merchantable quality is enhanced.

Still another object of the present invention is to provide a fraction apparatus for a penis in which the structure of receiving the glans before creating a vacuum has appropriate elasticity and is foldable so that application of the apparatus to the penis and removal thereof can be smoothly conducted, and the glans can be prevented from getting injured, thus enhancing the safety and reliability of the apparatus.

Still another object of the present invention is to provide a fraction apparatus for a penis in which the decompression body for receiving the glans has a shape corresponding to that of the glans so that the glans is reliably and easily supported by the decompression body and the anatomical shape of the glans can be maintained when it is extended, thus preventing the shape of the glans from being deformed.

Still another object of the present invention is to provide a fraction apparatus for a penis in which a base member which supports the longitudinal support member for applying tensile force to the penis has an elliptical shape which is open on a portion thereof, and the base member is configured in such a way that the open portion of the base member is disposed between the penis and the testicles, thus preventing the base member from coming into contact with the testicles, thereby enabling the user to put on the traction apparatus even in his daily routine.

Technical Solution

In order to accomplish the above object, in an aspect, the present invention provides a traction apparatus for a penis, including: a decompression unit receiving a glans of the penis therein and inflating the glans; a wearing unit comprising a belt wound around an upper body of a user, and a height adjustment plate connected to the belt, the height adjustment plate extending a predetermined length in a vertical direction in such a way that a height of the decompression unit is adjustable; and a connection unit coupled to the decompression unit and to the height adjustment plate so that the decompression unit is connected to the wearing unit by the connection unit.

In another aspect, the present invention provides a fraction apparatus for a penis, including: a base member having a predetermined shape so that the penis is inserted into the base member, the base member supporting a lower portion of the penis inserted thereinto; longitudinal support members coupled at first ends thereof to a base member, each of the longitudinal support members being adjustable in length; and a decompression unit receiving a glans of the penis therein and inflating the glans, the decompression unit being coupled to second ends of the longitudinal support members so that the decompression unit is supported by the longitudinal support members.

In another aspect, the present invention provides a fraction apparatus for a penis, including: a base member having a predetermined shape so that the penis is inserted into the base member, the base member supporting a lower portion of the penis inserted thereinto; longitudinal support members coupled at first ends thereof to a base member, each of the longitudinal support members being adjustable in length; a decompression unit receiving a glans of the penis therein and inflating the glans, the decompression unit being coupled to second ends of the longitudinal support members so that the decompression unit is supported by the longitudinal support members; a wearing unit comprising a belt wound around an upper body of a user, and a height adjustment plate connected to the belt, the height adjustment plate extending a predetermined length in a vertical direction in such a way that a height of the decompression unit is adjustable; and a connection unit coupled to the decompression unit and to the height adjustment plate so that the decompression unit is connected to the wearing unit by the connection unit.

The decompression unit may include: a decompression body receiving the glans of the penis therein; an elastic folded part made of an elastic material and provided around an opening of the decompression body in such a way that the elastic folded part is folded between an inside and an outside of the decompression body, the elastic folded part elastically supporting the penis; support rods extending in a longitudinal direction, each of the support rods having a first end into which the corresponding longitudinal support member inserted, with a spring provided in each of the support rods so that the support rod elastically supports the corresponding longitudinal support member; a body connector extending to opposite sides from the decompression body so that the decompression body is coupled to the support rods by the body connector; and an air suction valve sucking out air from the decompression body.

The body connector may be integrated with the decompression body and has in each of opposite side edges thereof an insert slot into which the corresponding support rod is fitted, and an insert flange may protrude from an outer surface of each of the support rods and be removably fitted into the corresponding insert slot of the body connector.

The base member may include: a curved part having a curved shape and supporting an outer surface of the penis; support protrusions extending from opposite sides of the curved part in such a way that distal ends thereof face each other; coupling protrusions protruding forwards from the base member between the curved part and the support protrusion, with a coupling hole formed in each of the coupling protrusion so that the first end of the corresponding longitudinal support member is inserted into the coupling hole; and an upper protruding support protruding forwards from an upper portion of the curved part, the upper protruding support supporting the penis.

Each of the longitudinal support members may include: a base coupling rod having a first end inserted into the base member, and a second end extending in the longitudinal direction; an insert rod into which the second end of the base coupling rod is inserted in such a way that the base coupling rod is movably coupled to the insert rod, with at least one fastening hole formed through an outer surface of the insert rod; and a receiving rod having a first end into which the insert rod is inserted in such a way that the insert rod is coupled to the receiving rod so as to be adjustable in a length of combination of the insert rod and the receiving rod, and a second end inserted into the decompression unit.

The base coupling rod may include: a base insert rod inserted at a first end thereof into the base member, with a locking protrusion provided on an outer surface of the base insert rod; a threaded extension rod extending from a second end of the base insert rod, with an external thread formed on an outer surface of the threaded extension rod so that the threaded extension rod is thread coupled to the insert rod; and a rotational knob fastened around a circumferential outer surface of the threaded extension rod so that a length to which the base coupling rod is extracted from the insert rod is adjusted by rotating the rotational knob.

The longitudinal support member may further include a coupling unit having a hole formed through the coupling unit in a longitudinal direction thereof so that the receiving rod is movably inserted into the hold of the coupling unit, with an internal thread formed on a circumferential inner surface of the coupling unit, and a stop ring protruding inwards from the circumferential inner surface of the coupling unit. The receiving rod may include: an end stopper thread-coupled to the second end of the receiving rod, the end stopper having a diameter greater than an inner diameter of the stop ring of the coupling unit so that the end stopper is stopped by the stop ring; and an external threaded ring provided on a circumferential outer surface of the first end of the receiving rod into which the insert rod is inserted, with a fastening ring threaded over the external threaded ring.

The longitudinal support member may further include an insert fastening unit coupled to the fastening hole via a circumferential outer surface of the receiving rod so that the insert rod is fastened to the receiving rod. The insert fastening unit may include: a fastening ring fastened to the circumferential outer surface of the receiving rod; and a fastening screw threaded into the fastening hole of the insert rod via the fastening ring so that the insert rod is fastened to the receiving rod.

The connection unit may include: a connection wire fastened to the decompression unit; and an elastic connection member connected to the connection wire and the wearing unit to provide an elastic restoring force.

The height adjustment plate may have a plurality of locking holes arranged in a longitudinal direction of the height adjustment plate, and the connection unit may be selectively locked to one of the locking holes so that a height at which the connection unit is locked to the height adjustment plate is adjusted.

Advantageous Effects

A traction apparatus for a penis according to the present invention can straighten the penis in one direction and has a length-adjustable structure. Thus, the apparatus can be used to treat penis plastica and microgenitalism. Further, the apparatus of the present invention can extend the glans of the penis using vacuum pressure and dull the sensitivity of the glans. Therefore, the apparatus can exhibit effects of treating premature ejaculation and microgenitalism.

Furthermore, in the present invention, a longitudinal support member and a wearing unit can apply tensile force to the penis, and the decompression unit can apply vacuum force to the glans of the penis, so that penis plastica, microgenitalism, and premature ejaculation can be treated at the same time. When the user continuously puts on the traction apparatus, the tissues, nerves and blood vessels of the penis are stimulated so that blood circulation is promoted, thus enhancing the erectility of the penis.

In the present invention, either of the wearing unit or the longitudinal support member may be used in penis traction, or all of them may be used. Therefore, even if one element is lost, the traction can be realized only by the other element. Of course when necessary, the user may selectively combine the elements, thus being more convenient for the user.

Furthermore, in the present invention, the wearing unit may be used in traction of penis. In this case, in response to the movement of the user's upper body, various traction force is applied to the penis and moves it, thus preventing and treating prostatitis.

In addition, the decompression body is removably coupled to a support rod so that both the decompression body and the wearing unit may be used, and the decompression body, the base member and the longitudinal support member may be selectively combined by the user. Therefore, the merchantable quality can be enhanced.

In the present invention, the glans which is received in the decompression body made of hard material can be supported by an elastic foldable structure. Hence, even when the glans which has expanded is pulled out of the decompression body, it can be smoothly removed therefrom without causing injury.

Further, the decompression body has a shape corresponding to that of the glans so that when the glans is inflated by vacuum force, the anatomical shape thereof can be maintained, thus preventing the shape of the glans from being deformed.

In addition, an elastic member made of silicone is provided on the opening of the decompression unit into which the glans is inserted, thus facilitating the insertion of the glans into the decompression unit. Because the elastic member forms a stepped portion, the glans is prevented from being undesirably removed from the decompression unit, regardless of the size of the glans. Moreover, when the user removes the glans which has been inflated by vacuum force from the decompression unit, the glans can be smoothly and painlessly removed therefrom.

In the present invention, after the traction apparatus is put on the penis, it may be supported by the wearing unit which is put on a portion of the user's body, such as the upper body or the neck. Therefore, the user can put on the traction apparatus in his daily routine, and the traction apparatus is prevented from being undesirably removed from the penis while putting it on.

DESCRIPTION OF DRAWINGS

FIGS. 11 and 12 are sectional views illustrating an insert fastening unit of the traction apparatus according to the present invention;

FIG. 13 is a sectional view illustrating an insert rod of the fraction apparatus according to the present invention;

FIG. 14 is a front view illustrating the use of a wearing unit of the traction apparatus according to the present invention;

DESCRIPTION OF THE ELEMENTS IN THE DRAWINGS

| | |
|---|---|
| 10: base member | 11: support protrusion |
| 12: upper protruding support | 13: coupling protrusion |
| 14: curved part | 15: parallel portion |
| 16: inclined portion | 20: longitudinal support member |
| 21: base coupling rod | 22: insert rod |
| 23: receiving rod | 24: coupling unit |
| 25: insert fastening unit | 30: decompression unit |
| 31: decompression body | 32: support rod |
| 33: body connector | 34: elastic folded part |
| 35: air suction valve | 40: connection unit |
| 41: elastic connection member | 42: connection wire |
| 50: wearing unit | 51: height adjustment plate |
| 52: belt | 53: first fastener |
| 54: buckle | 55: second fastener |
| 131: coupling hole | 211: rotational knob |
| 212: threaded extension rod | 213: base insert rod |
| 221: fastening hole | 222: stop protrusion |
| 231: external threaded ring | 232: end stopper |
| 241: stop ring | 242: internal thread |
| 251: fastening screw | 252: fastening ring |
| 253: slidegroove | 311: opening rim |
| 321: spring | 331: coupling hole |
| 511: locking hole | |

BEST MODE

Hereinafter, a preferred embodiment of a traction apparatus for a penis according to the present invention will be described in detail with reference to the attached drawings.

Figure 1:
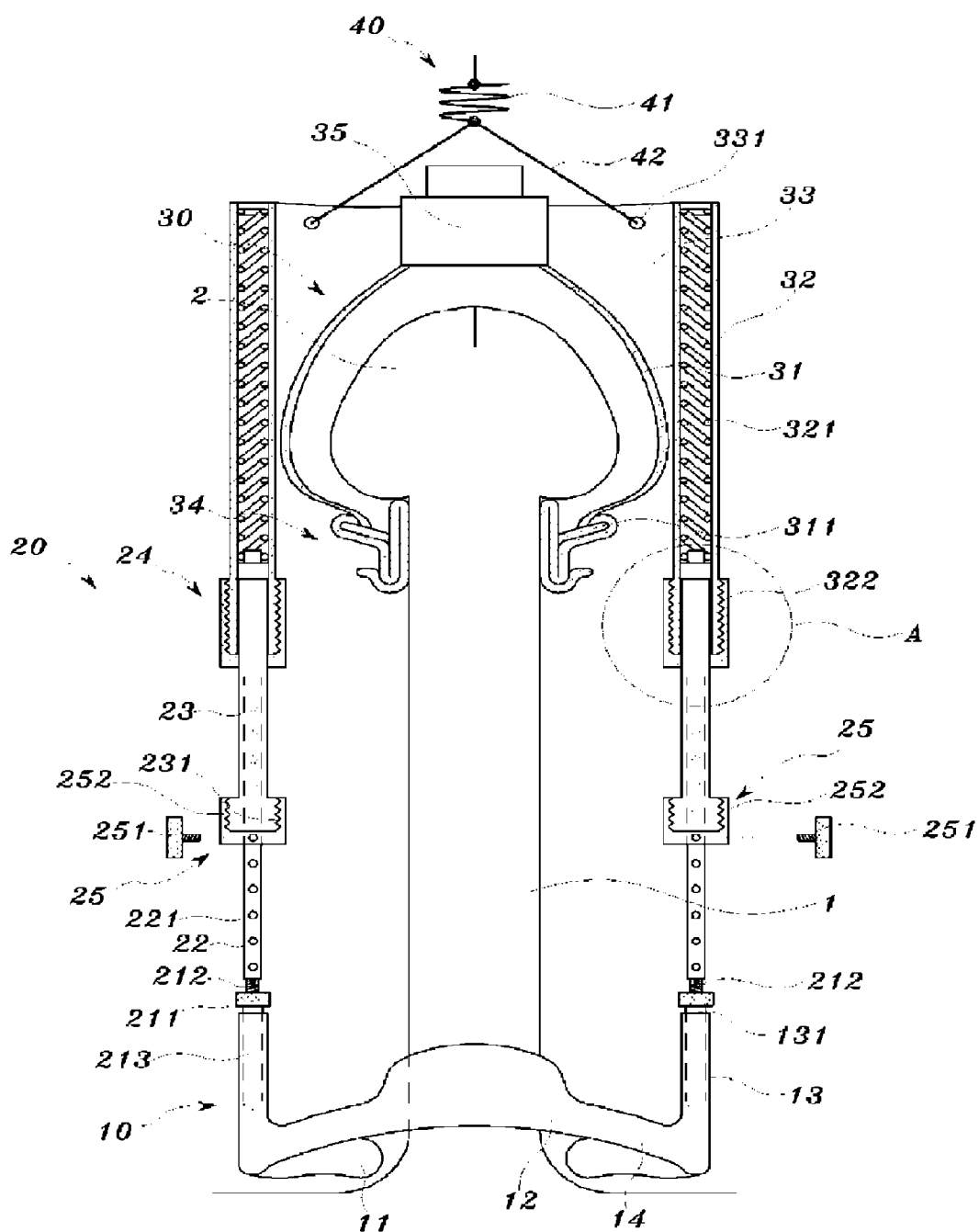
FIG. 1 is a plan view illustrating a traction apparatus for a penis, according to an embodiment of the present invention.

FIG. 1 is a plan view illustrating the traction apparatus according to the present invention.

Referring to FIG. 1, the traction apparatus according to the present invention includes a base member 10, longitudinal support members 20, a decompression unit 30 and a connection unit 40. The base member 10 supports a proximal end of the penis. The longitudinal support members 20 are connected to the base member 10 and are adjustable in length. The decompression unit 30 is fastened to the longitudinal support member 20, receives the glans of the penis and reduces pressure therein. The connection unit 40 is connected to the decompression unit 30 and fastened to a portion of the body of the user.

The base member 10 is located on the lower half of the user's body above his testes and supports the penis inserted thereinto. The base member 10 has a generally elliptical shape which is open on a corresponding portion thereof so that when the user sits down and stands up, the base member 10 is prevented from striking or pressing the testes.

Each longitudinal support member 20 comprises at least one or more rods which are connected to each other in multistage so that the longitudinal support member 20 can be adjusted in length by extending or contracting it in a telescopic manner. Thus, the longitudinal support members 20 are coupled to the decompression unit 30 and the base member 10 and apply force to the penis so that the length of the penis is extended.

The decompression unit 30 is fastened to the longitudinal support members 20. The decompression unit 30 receives the glans 2 of the penis therein and inflates the glans 2 by reducing the pressure in the decompression unit 30, thus dulling the sensitivity of the glans 2 to cure premature ejaculation. Preferably, the decompression unit 30 creates a vacuum therein to inflate the glans 2.

Furthermore, although not shown in FIG. 1, the present invention further includes a wearing unit 50 which is coupled to the depression unit 30 and is put on the upper body of the user so that the longitudinal support member 20 and the decompression unit 30 are fastened to the body of the user. The wearing unit 50 will be explained in detail later herein with reference to FIGS. 14 and 15. The decompression unit 30 may be supported both by the longitudinal support member 20 and by the wearing unit 50, alternatively, or it may be supported by either of them according to the selection of the user. The decompression unit 30 will be described in detail with reference to FIGS. 1 and 2.

Figure 2:
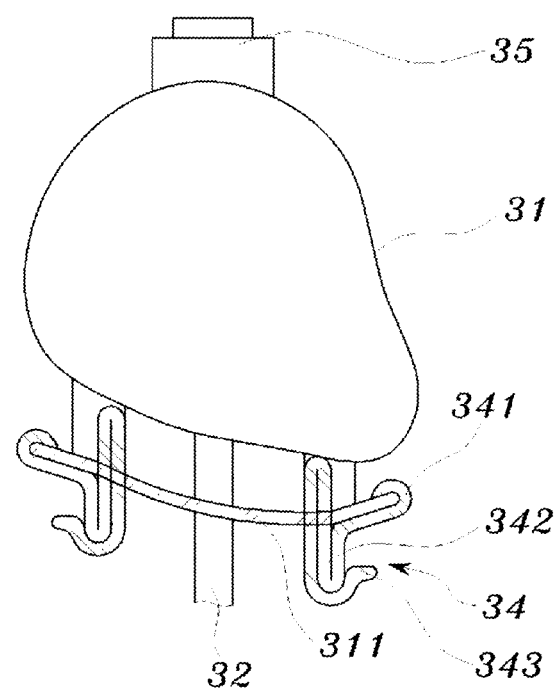
FIG. 2 is a side sectional view of a decompression unit of the traction apparatus according to the present invention.

FIG. 2 is a side sectional view of the decompression unit of the traction apparatus according to the present invention Referring to FIG. 2, the decompression unit 30 includes a decompression body 31, support rods 32, a body connector 33, an elastic folded part 34 and an air suction valve 35. The decompression body 31 receives the glans of the penis and reduces the pressure therein to inflate the glans. The support rods 32 support the decompression body 31 on opposite sides of the decompression body 31. The body connector 33 connects the support rod 32 to the decompression body 31. The elastic folded part 34 elastically contracts an opening of the decompression body 31. The air suction valve 35 is provided on the decompression body 31 and allows air to be drawn into the decompression body 31 to release the vacuum in the decompression body.

Preferably, the decompression body 31 has an anatomical shape corresponding to that of the glans 2 of the penis. The decompression body 31 is formed by injection molding using hard material to prevent the glans 2 from being deformed while being expanded by suction pressure in the vacuum. The decompression body 31 includes an opening rim 311 which is formed by the injection molding so that the opening of the decompression body 31 is defined by the opening rim 311. It is preferable that oil, other lotion, or the like be applied to the glans 2 before it is inserted into the decompression body 31.

The opening rim 311 forms the opening of the decompression body 31 and has a ring shape which is formed along a circumferential edge of a bottom end of the decompression body 31 and extends a predetermined width around the opening, thus supporting the elastic folded part 34.

The elastic folded part 34 is made of elastic material, for example, a silicone band. The silicone band having a predetermined thickness and length includes a first edge 341 which is fastened to a circumferential outer edge of the opening rim 311 in such a way that the first edge 341 wraps the circumferential outer edge of the opening rim 311 in a 'U' shape. The silicone band further includes a medial portion 342 which extends from the first edge 341 and is integrally folded in several times between the inside and the outside of the decompression body 31, and a second edge 343 which extends from the medial portion 342 to the outside of a lower bent portion of the medial portion 342. This will be explained in more detail with reference to FIGS. 3 through 5.

Figure 3:
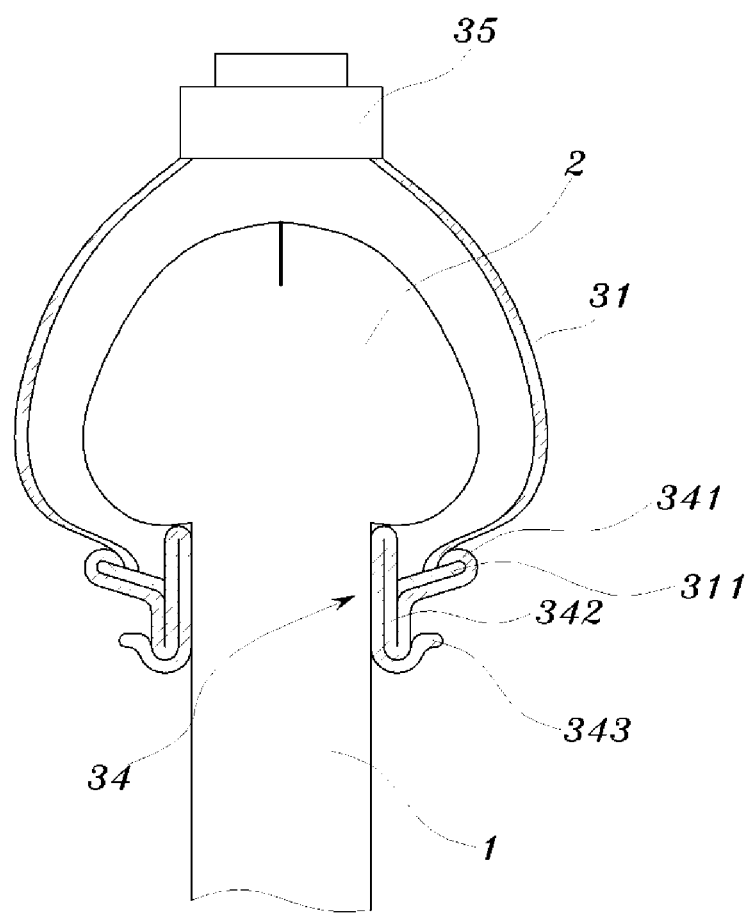
FIGS. 3 through 5 are side sectional views showing the operation of an elastic folded part of the decompression unit of the traction apparatus according to the present invention.
Figure 4:
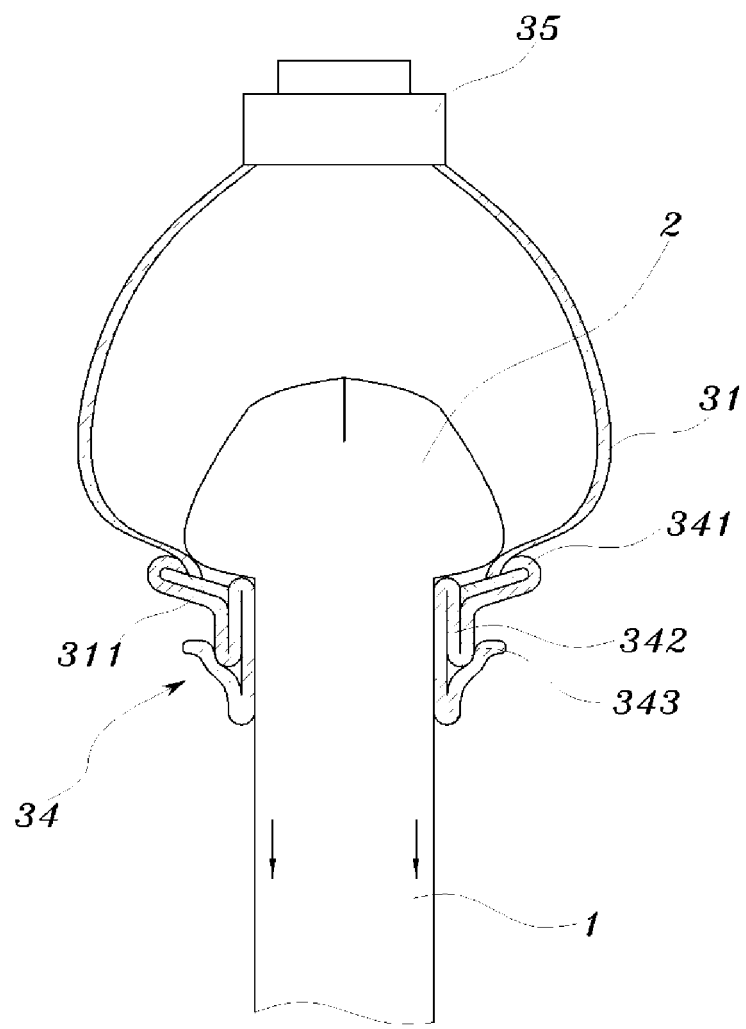
Figure 5:
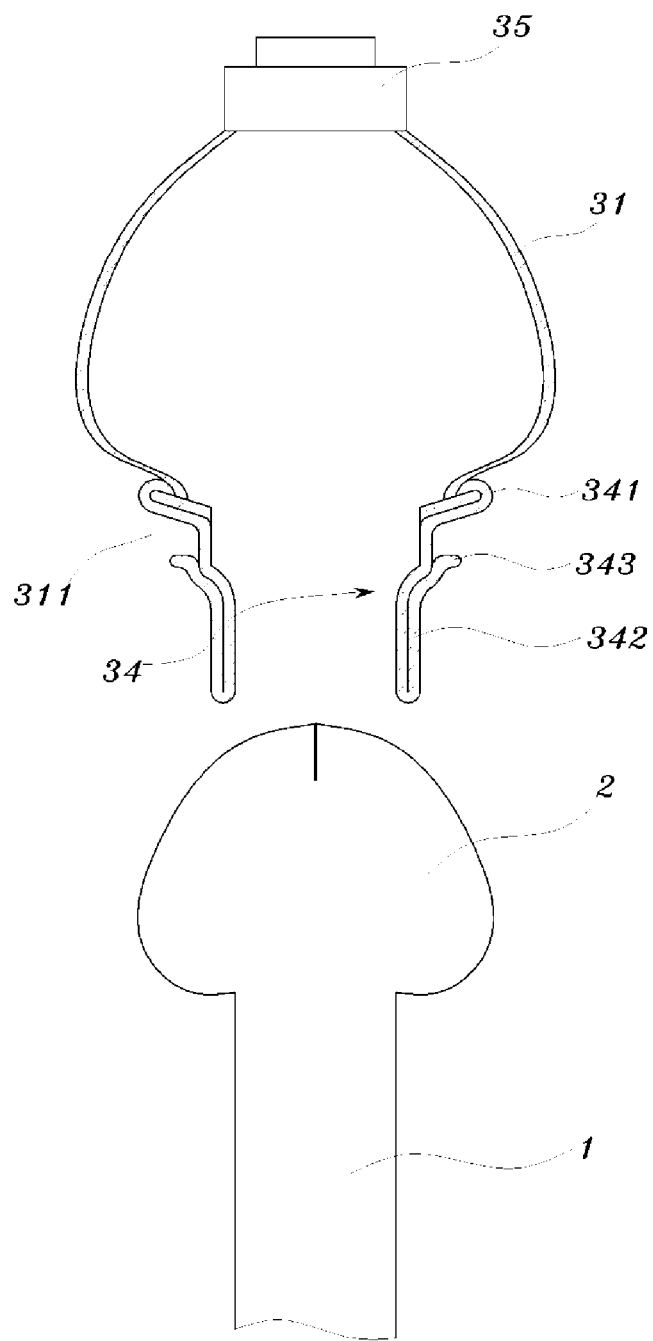

FIGS. 3 through 5 are side sectional views showing the operation of the elastic folded part of the decompression unit of the traction apparatus according to the present invention.

Referring to FIG. 3, as stated above, the elastic folded part 34 is configured in such a way that the first edge 341 is fastened to the opening rim 311 of the decompression body 31 and the medial portion 342 is turned up into the opening of the decompression body and turned down outside the opening to form the folded structure while the second edge 343 is disposed below the first edge 341. In other words, in the elastic folded part 34, the first edge 341 and the second edge 343 are located outside the opening of the decompression body, and the medial portion 342 that is folded by turning up and turning down is located inside the opening of the decompression body.

The medial portion of the elastic folded part 34 that is turned up and turned down is fastened to the opening rim 311 with the folded state. When the glans 2 is inserted into the decompression body 31, the elastic folded part 34 supports the glans 2 while it is in the folded state. The glans 2 can be inserted into the decompression body 31 without being injured because it is supported by the elastic folded part 34 having elasticity. The glans 2 that is inserted into the decompression body 31 is caught by the opening rim 311 which is comparatively hard and has a diameter smaller than that of the internal receiving space of the decompression body 31. Here, an undulating portion between the glans 2 and the penis shaft 1 is in minimal contact with a turndown end of the elastic folded part 34 so that the glans 2 is prevented from being injured by a close contact.

After the glans 2 has been inserted into the decompression body, an air suction device (not shown) is connected to the air suction valve 35 and sucks out air from the internal space of the decompression body 31, thus creating a vacuum in the decompression body. Then, the glans 2 is expanded in the vacuum. During this process, the glans 2 is prevented from being deformed even though it is expanded, because the glans 2 is supported by the decompression body 31 that is made of hard material and has the shape corresponding to the glans 2.

The glans 2 that is inserted into the decompression body 31 is caught by the elastic folded part that has the turndown portion in the decompression body 31, so that the glans 2 is prevented from being undesirably removed from the decompression body 31. On the other hand, when the glans 2 is removed from the decompression body 31 by the intention of the user, the glans 2 can be removed therefrom while maintaining the state in which the penis shaft 1 is in contact with the circumferential inner surface of the turndown portion of the medial portion 342 of the elastic folded part 34. That is, while the glans 2 is removed from the decompression body 31, the elastic folded part is elastically changed in shape in such a way that the turnup portion and the turndown portion of the elastic folded part which have been in slidable contact with each other slip relative to each other and that the length of the junction between the turnup portion and the turndown portion is reduced. Therefore, the glans 2 can be smoothly pulled out of the decompression body 31 without getting injured. Meanwhile, more preferably, oil or lotion is applied to the glans 2 before the glans 2 is inserted into the decompression body 31.

This will be explained in more detail with reference to FIG. 4. When the air suction valve 35 is open, the decompression body 31 releases the vacuum as air is drawn into the decompression body 31. Thereafter, the user pulls out the glans 2 from the decompression body 31. At this time, the medial portion 342 of the elastic folded part 34 that has been folded is moved in a slipping manner in the direction opposite to the direction in which it is folded, while the medial portion 342 supports the penis shaft that has been contained in the decompression body 31. Eventually, the medial portion 342 that has been folded is unfolded, as shown in FIG. 5.

Referring to FIG. 5, when the glans 2 that is being pulled out of the decompression body 31 passes a stepped portion formed by the opening rim 311, the glans 2 is elastically supported by the elastic folded part 34 that is being unfolded as the glans 2 moves. Therefore, the glans 2 can be smoothly pulled out of the decompression body 31 without getting injured.

Meanwhile, the body connector 33 has a planar shape having a predetermined thickness and is integrally formed with the decompression body 31 by injection molding. The body connector 33 connects the decompression body 31 to the support rods 32 in such a way that the body connector 33 is fastened to the outer surfaces of the support rods 32. In detail, the body connector 33 has coupling holes 331 to which a connection wire 42 of the connection unit 40 is coupled, and 'T'-shaped insert slots 332 which are formed in respective opposite side edges of the body connector 33. In this embodiment although the insert slot 332 is illustrated as having a 'T' shape, it may be formed in a circular or other shape.

The coupling holes 331 are formed through the body connector 33 at respective opposite sides of the decompression body 31. The connection wire 42 of the connection unit 40 is coupled to the coupling holes 331. A first end of the connection wire 42 is coupled to the coupling holes 331, and a second end thereof is supported by a body part of the user so that the decompression unit 30 and the longitudinal support members 20 are fastened to the body of the user in such a way that they are oriented in a predetermined direction.

The 'T'-shaped insert slots 332 are formed in the respective opposite side edges of the body connector 33 and extend from a top end to a bottom end of the body connection 33. Insert flanges 323 are removably inserted into the bottom ends of the corresponding insert slots 332. In detail, each insert slot 332 is closed on the top end thereof to prevent the insert flanges 323 from being moved relative to the insert slots 332 by the elastic force of springs 321 which are installed in the support rods 32. In addition, each insert slot 332 is open on the bottom end thereof so that the corresponding insert flange 323 can be inserted into or removed from the insert slot 332 through the bottom end thereof. Therefore, the support rods 32 can be separated from the body connector 33 as necessary.

Next the structure of coupling the insert flange 323 to the insert slot 332 will be described with reference to FIG. 6.

Figure 6:
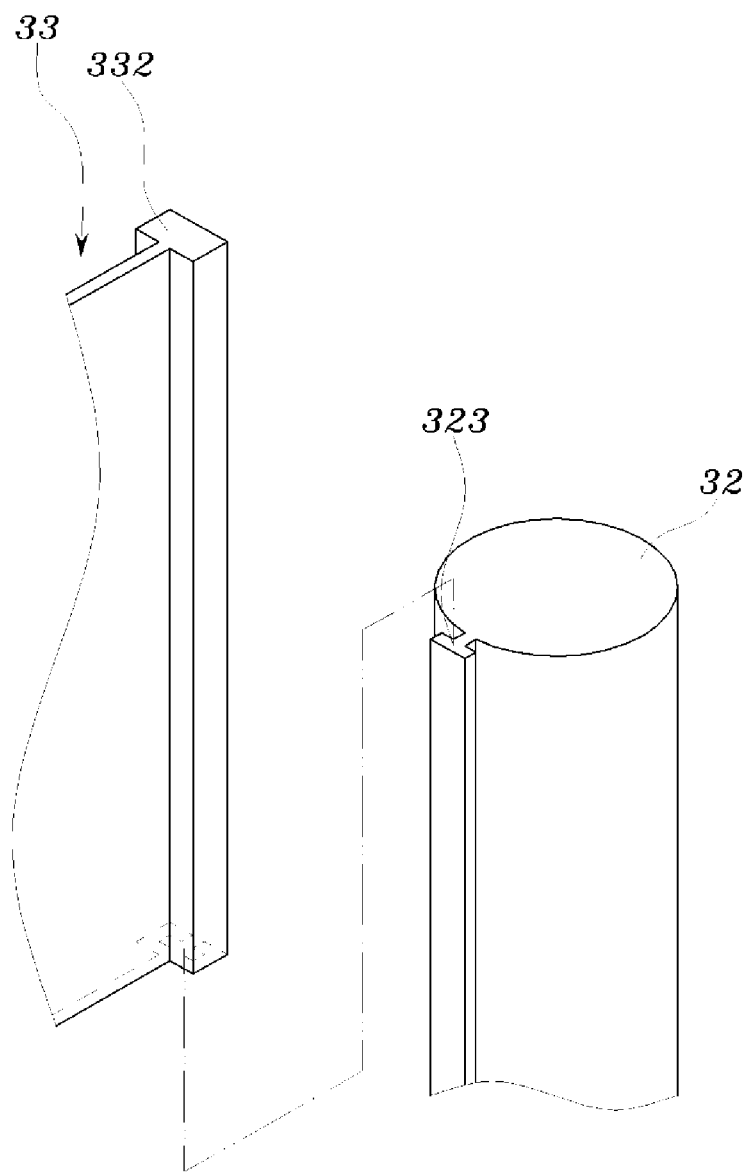
FIG. 6 is a partial perspective view showing the coupling of a body connector to a support rod of the traction apparatus according to the present invention.

FIG. 6 is a perspective view showing the coupling of the body connector to the support rod of the traction apparatus according to the present invention.

Referring to FIG. 6, the support rod 32 has a cylindrical rod shape. In the embodiment, the two support rods 32 are disposed on opposite sides of the decompression body 31 and coupled to the decompression body 31 by the body connector 33 to support the decompression body 31. For this, each support rod 32 includes the spring 321, a support coupling part 322 and the insert flange 323. The spring 321 is installed in a hollow space of the support rod 32 in such a way that the length thereof is elastically varied in response to a variation in the length of the longitudinal support member 20. The support coupling part 322 is thread-coupled to the corresponding longitudinal support member 20 which is inserted into a bottom end thereof. The insert flange 323 protrudes from the support rod 32 and is removably inserted into the corresponding insert slot 332.

In the present invention, the support rod 32 is removably coupled to the insert fastening unit 25 by the support coupling part 322. Therefore, traction of the penis can be conducted only by combining the wearing unit 50 with the decompression unit 30 without using the longitudinal support member 20, or by combining the longitudinal support members 20, the decompression unit 30, the base member 10 and the connection unit 40 with each other.

The spring 321 is installed in the corresponding support rod 32 and elastically supports a corresponding receiving rod 23 which is inserted into the bottom end of the support rod 32. Due to this structure, after the glans 2 has been inserted into the decompression body 31 and the longitudinal support members 20 have been set to a predetermined length, even if an external shock is applied to the traction apparatus or the length of the penis is varied by an erection, the lengths of the longitudinal support members 20 can be elastically varied. Furthermore, even though the longitudinal support members 20 are suddenly extended or contracted, the springs 321 elastically absorb force or pressure applied to the penis so that constant traction force is applied to the penis.

Each support rod 32 has the insert flange 323 which protrudes from the outer surface thereof. The insert flange 323 has a "T"-shaped cross-section and extends from the top end to the bottom end of the support rod 32. The insert flange 323 is inserted into the corresponding insert slot 332 through the open bottom end of the insert slot 332 and stopped by the closed top end of the insert slot 332. Thus, the support rod 32 is can be separated from the body connection 33 when necessary (refer to FIG. 6).

The air suction valve 35 is provided on the top end of the decompression body 31 and controls inflow of external air thereinto or outflow of the internal air therefrom. In detail, after the glans has been inserted into the decompression body 31, the air suction valve 35 allows air to be sucked out of the decompression body 31 to create a vacuum and then maintains the vacuum. When the air suction valve 35 is open, external air is drawn into the decompression body 31, thus releasing the vacuum. The air suction valve 35 is similar to that of a well-known vacuum suction cup. An air suction device (not shown) which has the same structure as that used for the vacuum suction cup is connected to the air suction valve 35 to suck air out of the decompression body.

The base member 10 is an injection-molding production which is formed into a single body and is made of synthetic material harmless to the human body. The base member 10 supports the proximal end of the penis, that is, the root portion of the penis which is just above the testicles. This has the shape as shown in FIGS. 7 and 8.

Figure 7:
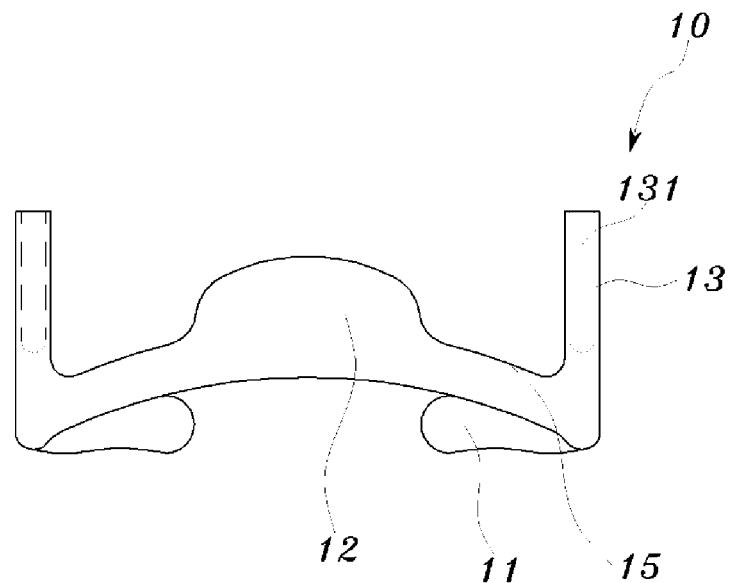
FIG. 7 is a perspective view illustrating a base member of the traction apparatus according to the present invention.

FIG. 7 is a perspective view illustrating the base member of the traction apparatus according to the present invention. FIG. 8 is a plan view of the base member of the traction apparatus according to the present invention.

Figure 8:
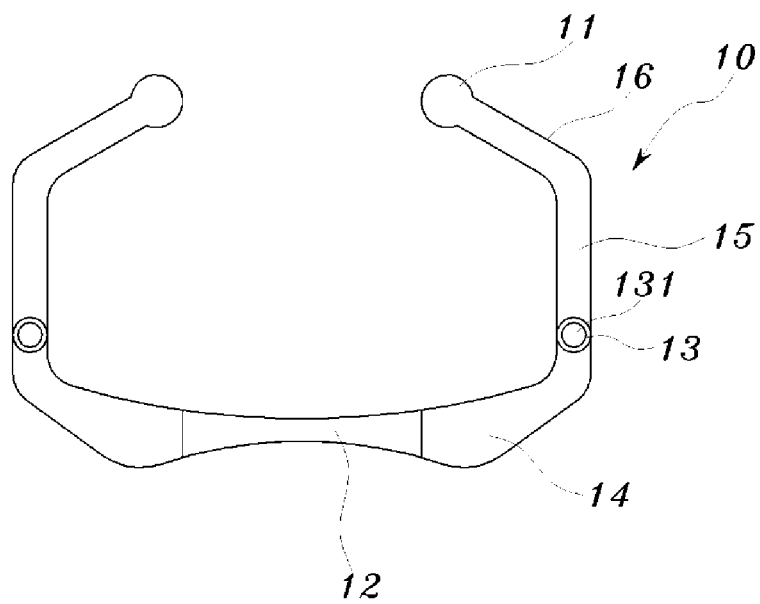
FIG. 8 is a plan view of the base member of the traction apparatus according to the present invention.

Referring to FIGS. 7 and 8, the base member 10 includes a curved part 14, an upper protruding support 12, parallel portions 15, coupling protrusions 13 and support protrusions 11.

The curved part 14 has a rim shape corresponding to the circumferential outer surface of the penis. The upper protruding support 12 protrudes from the curved part 14 upwards and supports the upper portion of the penis. The parallel portions 15 extend from the opposite sides of the curved part 14 in horizontal directions and have bent shapes. The coupling protrusions 13 protrude from the respective parallel portions 15 towards the distal end of the apparatus. The longitudinal support members 20 are coupled to the respective coupling protrusions 13. The support protrusions 11 are provided on the ends of the respective parallel portions 15 that extend downwards at predetermined inclined angles.

The support protrusions 11 comprise two circular protrusions which are disposed at positions facing each other with space defined therebetween. The support protrusions 11 support the lower portion of the penis shaft 1 of which the upper portion is seated onto the curved part 14. In the present invention, because the space is formed between the support protrusions 11, not only when the user who wears the traction apparatus is in action but also even if the time during which the user wears it is comparatively long, pain can be prevented from occurring. Furthermore, when the user wears the traction apparatus, the penis can be prevented from coming into contact with the base member, because the penis can be inserted into the traction apparatus through the space between the support protrusions 11.

The curved part 14 has a rim shape which is convex upwards and is curved to correspond to the circumferential outer surface of the penis. The curved part 14 is spaced apart from the support protrusions 11 so that a predetermined space is defined between the curved part 14 and the support protrusions 11. The penis is inserted between the curved part 14 and the support protrusions 11 so that the penis is supported on the lower portion thereof by the support protrusions 11 and supported on the upper portion thereof by the curved part 14.

The upper protruding support 12 protrudes from the upper surface of the curved part 14 upwards and has front and rear surfaces having a predetermined a width. The upper protruding support 12 supports the skin of the upper portion of the penis which is disposed between the curved part 14 and the support protrusions 11.

The parallel portions 15 extend from the opposite sides of the curved part 14 downwards in a direction perpendicular to the curved part 14 and are parallel to each other so that they stably surround the penis. Preferably, unlike the curved part 14 extending in the horizontal direction, the parallel portions 15 extend in the vertical direction to have shapes corresponding to the shapes of the opposite side portions of the penis.

Each coupling protrusion 13 protrudes from a front surface of the corresponding parallel portion 15 forwards. A coupling hole 131 is formed in each coupling protrusion 13 so that a corresponding base coupling rod 21 which will be explained later herein is inserted into the coupling hole 131. As such, the coupling protrusions 13 protrude from the respective parallel portions 15 which are disposed on opposite sides of the base member and extend from the opposite ends of the curved part 14.

An inclined portion 16 extends from each parallel portion 15 downwards at a predetermined angle so that it corresponds to the outer surface shape of the penis.

The support protrusions 11 each of which has a circular protrusion shape are provided on the ends of the corresponding inclined portions 16 at positions that face each other and are spaced apart from each other by a predetermined distance. In this embodiment, the support protrusions 11 which are provided on the ends of the respective opposite inclined portions 16 define therebetween the opening section of the base member 10 which has an elliptical shape.

If the base member 10 has a closed elliptical shape unlike the present invention having the opening between the support protrusions 11, when the user wears the traction apparatus, the base member having the closed elliptical shape surrounds and presses the testicles, thus causing pain in the testicles when the user sits down or stands up.

In the present invention, the base member 10 has the opening between the support protrusions 11 which are disposed below the testicles. Thus, when the user sits down or stands up, the testicles are prevented from coming into contact with the base member 10. Therefore, the user who wears the traction apparatus can walk or move without discomfort.

Next the longitudinal support member will be described in detail with reference to FIGS. 1 and 9 through 13.

Figure 9:
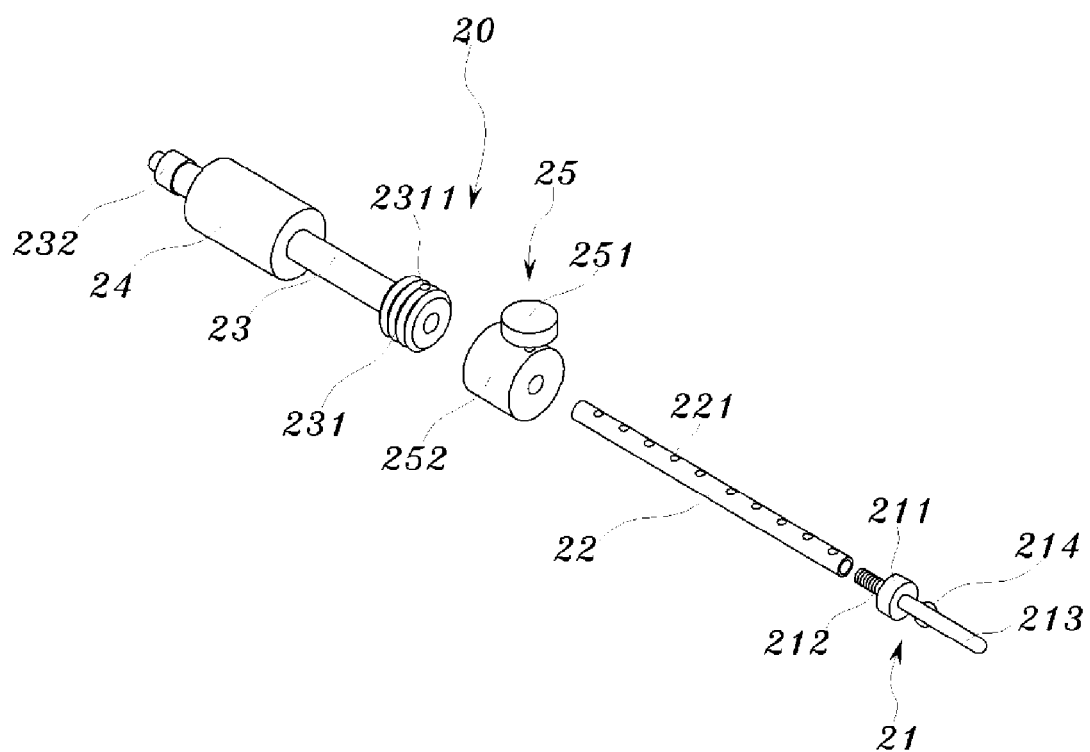
FIG. 9 is an exploded perspective view of a longitudinal support member of the base member of the traction apparatus according to the present invention.
Figure 10:
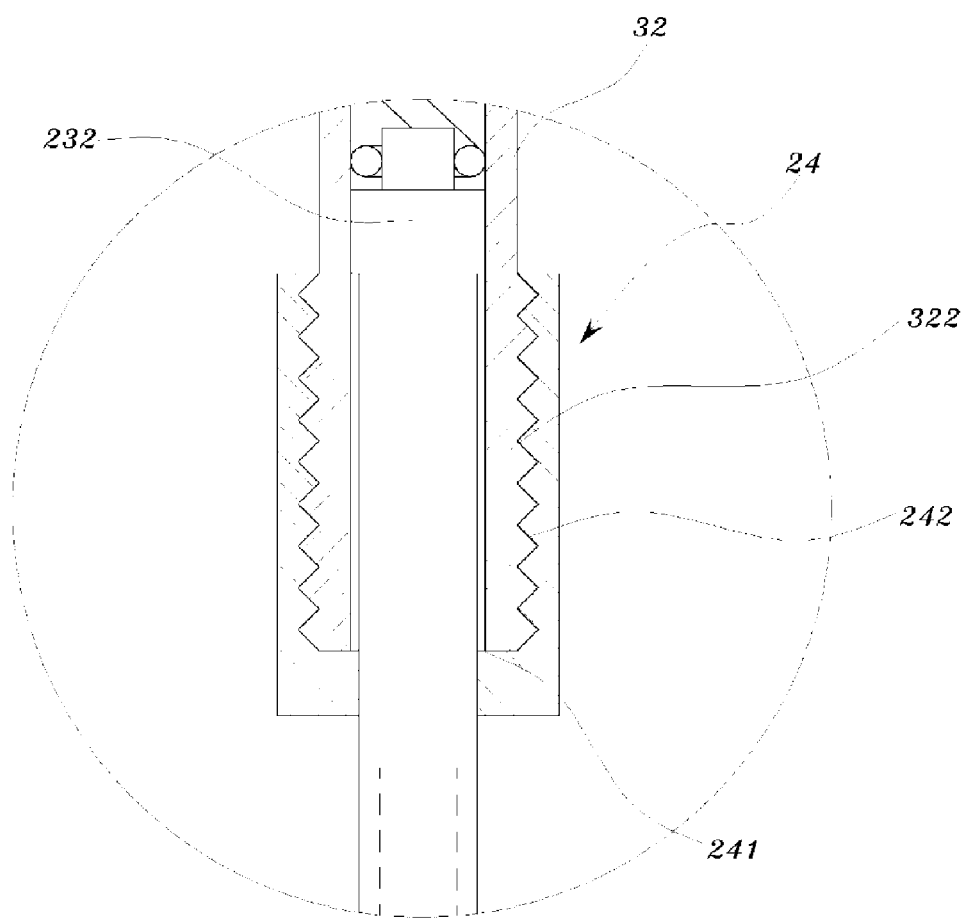
FIG. 10 is an enlarged view of circled portion A of FIG. 1.
Figure 11:
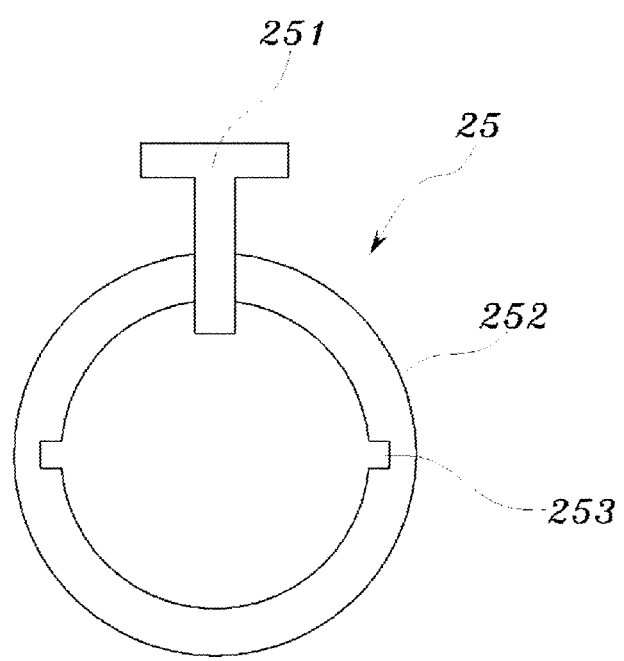
Figure 1:
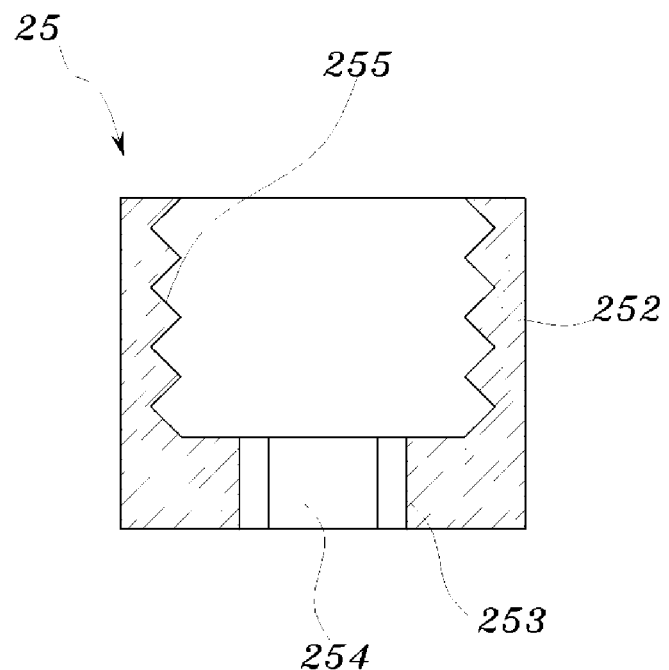
Figure 1:
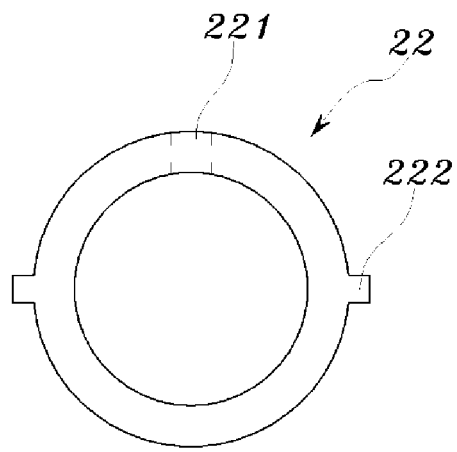
Figure 1:
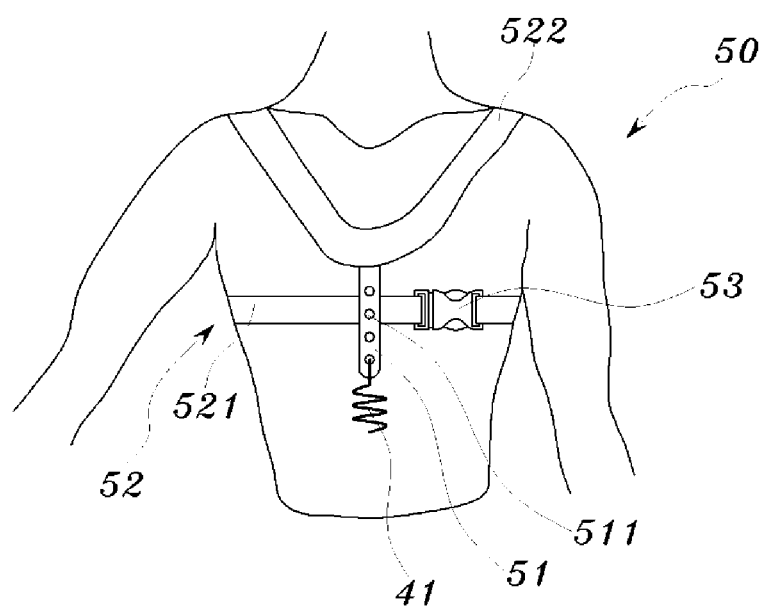

FIG. 9 is an exploded perspective view of the longitudinal support member of the base member of the traction apparatus according to the present invention. FIG. 10 is an enlarged view of circled portion A of FIG. 1. FIGS. 11 and 12 are sectional views illustrating the insert fastening unit. FIG. 13 is a sectional view illustrating an insert rod.

Each longitudinal support member includes the base coupling rod 21 which is coupled to the base member 10, and the insert rod 22 which has a rear end coupled to the base coupling rod and a front end removably inserted into the support rod. The longitudinal support member further includes the receiving rod 23 into which the front end of the insert rod is inserted 22, a coupling unit 24 which is provided on a front end of the receiving rod and coupled to the decompression unit 30, and the insert fastening unit 25 which fastens the receiving rod 23 to the insert rod 22.

The base coupling rod 21 includes a threaded extension rod 212 which is inserted into the insert rod 22 and moves the insert rod 22 in the longitudinal direction to vary the length thereof, a base insert rod 213 which is inserted into the base member 10, and a rotational knob 211 which adjusts the length to which the threaded extension rod 212 extends.

The base insert rod 213 is inserted into the corresponding coupling hole 131 of the base member 10 and is rotatably locked thereto by a locking protrusion 214 which is provided on the outer surface of the base insert rod 213. Thus, when the rotational knob 211 rotates, the base insert rod 213 can rotate on its own axis but be prevented from be pulled out of the base member 10 because the base insert rod 213 is locked to the base member 10 by the locking protrusion 214.

The threaded extension rod 212 which is provided on the front end of the base insert rod 213 has on the circumferential outer surface thereof an external thread which engages with an internal thread formed on the inner surface of the insert rod 22 so that the entire length of the threaded extension rod 212 and the insert rod 22 that are connected to each other can be varied.

The rotational knob 211 is fastened around the threaded extension rod 212 so that rotating force is transmitted to the threaded extension rod 212 by rotating the rotational knob 211. Therefore, when the rotational knob 211 rotates, the threaded extension rod 212 is threaded along the internal thread formed on the inner surface of the insert rod 22. Thus, depending on the direction in which the rotational knob 211 rotates, the threaded extension rod 212 is extracted from or retracted into the insert rod 22 to extend or contract in length. Here the base insert rod 213 is inserted into the coupling hole 131 without thread coupling and is prevented from being removed from the coupling hole 131 by the locking protrusion 214. Hence, when the rotational knob 211 rotates, the base insert rod 213 only rotates on its own axis, but the threaded extension rod 212 is rotated along the internal thread of the insert rod 22 by the rotation of the rotational knob 211 and simultaneously extracted from or retracted into the insert rod 22.

The insert rod 22 has on the inner surface thereof the internal thread which engages with the threaded extension rod 212. A plurality of fastening holes 221 is formed through the circumferential outer surface of the insert rod 22 so that the insert fastening unit 25 is locked to a selected one of the fastening holes 221. Stop protrusions 222 are provided at opposite sides on the circumferential outer surface of the insert rod 22. The receiving rod 23 will be described in detail with reference to FIGS. 10 and 13.

The fastening holes 221 are formed in the circumferential outer surface of the insert rod 22 at positions spaced apart from each other at regular intervals in the longitudinal direction of the insert rod 22. A fastening screw 251 of the insert fastening unit 25 which will be explained later herein is tightened into a selected one of the fastening holes 221 through the receiving rod 23. Here the insert rod 22 is fastened to the receiving rod 23 by tightening the fastening screw 251 of the insert fastening unit 25 into the selected fastening hole 221. The length to which the insert rod 22 is extracted from the insert fastening unit 25 is determined by the position at which the fastening screw 251 is tightened into a selected one of the fastening holes 221.

The stop protrusions 222 are provided on the outer surface of the insert rod 22 and locked to the inner surface of the insert fastening unit 25 to prevent the insert rod 22 from rotating. The detailed operation of the stop protrusions 222 will be explained later herein in the description of the insert fastening unit 25.

The receiving rod 23 has a rod shape and includes a rear end into which the front end of the insert rod 22 is inserted, and a front end which is inserted into the support rod 32. An end stopper 232 is provided on the front end of the receiving rod 23 and locked to an inner surface of a rear end of the coupling unit 24 to prevent the receiving rod 23 from being removed from the coupling unit 24. In the embodiment, to prevent the receiving rod 23 from being completely removed from the coupling unit 24 while it can move in the longitudinal direction along the circumferential inner surface of the coupling unit 24, a stop ring (241, refer to FIG. 10) protrudes from the circumferential inner surface of the rear end of the coupling unit 24 so that the end stopper (232, refer to FIG. 10) of the receiving rod 23 is stopped by the stop ring 241.

Furthermore, the receiving rod 23 further includes an external threaded ring 231 which protrudes around the circumferential outer surface of the rear end of the receiving rod 23 and is threaded into the inner surface of the insert fastening unit 25.

The external threaded ring 231 protrudes around the outer surface of the rear end of the receiving rod 23 into which the insert rod 22 is inserted. The external threaded ring 231 is threaded with an internal thread formed in a receiving depression 255 of the insert fastening unit 25.

The insert fastening unit 25 includes a fastening ring 252 which is fitted over the outer surface of the receiving rod. The receiving depression 255 is formed in the fastening ring 252 and has therein the internal thread which engages with the external threaded ring 231 to couple the fastening ring 252 to the receiving rod 23. A passing hole 254 is formed through the rear end of the fastening ring 252 and communicates with the receiving depression 255. The insert rod 22 is inserted into the passing hole 254 so as to be movable in the longitudinal direction. Slide grooves 253 are formed in the inner surface of the passing hole 254 so that the stop protrusions 222 are inserted into the corresponding slide grooves 253 and are slidable along the slide grooves 253. The insert fastening unit 25 further includes the fastening screw 251 which is threaded both into the circumferential outer surface of the fastening ring 252 and into one of the fastening holes 221 of the insert rod 22, thus fastening the fastening ring 252 to the insert rod 22.

The fastening ring 252 is coupled to the rear end of the receiving rod 23 by tightening the external threaded ring 231 of the receiving rod 23 into the receiving depression 255 of the fastening ring 252. The insert rod 22 is inserted into the receiving rod 23 via the passing hole 254 in such a way that the stop protrusions 222 are inserted into the corresponding slide grooves 253 formed in the passing hole 254 of the insert fastening unit. The insert rod 22 is guided not only by the passing hole 254 of the fastening ring 252 but also by sliding the stop protrusions 222 along the slide grooves 253. Thus, the insert rod 22 is moved only in the linear direction without rotating. Furthermore, the fastening screw 251 is tightened into one of the fastening screws 251 through the circumferential surface of the fastening ring 252, thus determining the length to which the insert rod 22 is inserted into the receiving rod 23.

The slide grooves 253 into which the stop protrusions 222 are inserted linearly extend in the longitudinal direction, so that even when the fastening screw 251 is not tightened into the selected fastening hole 221, the insert rod 22 cannot rotate. Moreover, because the insert rod 22 is prevented from rotating due to the insertion of the stop protrusions 222 into the slide grooves 253, aligning the fastening screw 251 with the selected fastening hole 221 can be further facilitated.

Therefore, the user adjusts the distance that the insert rod 22 is extracted from the receiving rod 23 in such a way that the insert rod 22 is extracted from or retracted into the receiving rod 23 depending on the length of his own penis. Thereafter, the fastening screw 251 is tightened into one of the fastening holes 221 of the insert rod 22 that corresponds to the adjusted distance. Thereby, the insert rod 22 is fastened to the receiving rod 23.

Meanwhile, a longitudinal hole formed through the coupling unit 24 so that the receiving rod 23 is inserted through the coupling unit 24 so as to be movable in the longitudinal direction. An internal thread 242 is formed on the inner surface of the coupling unit 24 and threaded over the support coupling part 322 provided on the circumferential outer surface of the rear end of the support rod 32. Furthermore, the coupling unit 24 has the stop ring 241 which protrudes from the rear end of the coupling unit 24 towards the central axis thereof so that the end stopper 232 is stopped by the stop ring 241. Thereby, the receiving rod 23 is prevented from being completely removed from the coupling unit 24.

Next the connection unit will be described in detail.

The connection unit 40 includes the connection wire 42 which is connected to the body connector 33, and an elastic connection member 41 which elastically supports the upper end of the connection wire 42.

The rear end of the connection wire 42 is fastened to the coupling holes of the body connector 33, and the front end thereof is coupled to a rear end of the elastic connection member 41, thus holding the body connector 33 which supports the decompression body 31.

The elastic connection member 41 comprises a coil-shaped member having appropriate elasticity like the spring 321. The elastic connection member 41 elastically supports the connection wire 42 connected to the rear end thereof. A front end of the elastic connection member 41 is locked to a height adjustment plate 51 which will be described later herein.

The connection unit 40 having the above-mentioned construction is coupled to the wearing unit 50 which is put on the chest and the neck of the upper body of the user, so that the decompression body 31 can be oriented in one direction and maintained in the oriented state. Hereinafter, the wearing unit 50 will be explained in detail with reference to FIGS. 14 and 15.

Figure 15:
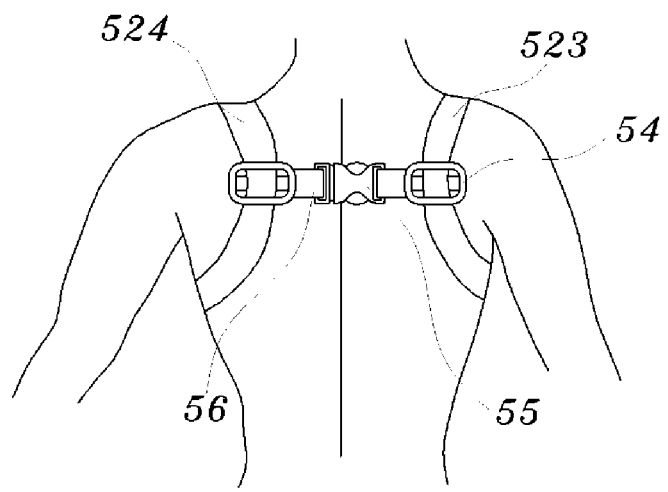
FIG. 15 is a rear view illustrating the use of the wearing unit of the traction apparatus according to the present invention.

FIG. 14 is a front view illustrating the use of the wearing unit of the traction apparatus according to the present invention. FIG. 15 is a rear view illustrating the use of the wearing unit of the traction apparatus according to the present invention.

Referring to FIGS. 14 and 15, the wearing unit 50 includes the height adjustment plate 51 to which a hook is hooked, a belt 52 which is wound around the upper body of the user along his shoulders and the chest, and a first fastener 53 which couples both ends of the belt 52 to each other on the front surface o the user. The wearing unit 50 further includes a second fastener 55, buckles 54 which couple the second fastener 55 to the belt 52 and are adjustable in positions upwards or downwards so that the distance between both sides of the belt on the back of the user can be adjusted depending on the length and width of the upper body of the user, and buckle connection members 56 which couple the corresponding buckles 54 to the second fastener 55.

In detail, locking holes 511 are formed through the height adjustment plate 51 and arranged in the longitudinal direction thereof. The elastic connection member 41 is hooked to a selected one of the locking holes 511. Therefore, the user can appropriately adjust the height at which the elastic connection member 41 is locked to the height adjustment plate 51 depending on his own body size.

In the present invention, the elastic connection member 41 is hooked to the height adjustment plate 51, and the tensile force applied to the penis can be adjusted depending on the height at which the elastic connection member 41 is hooked to the height adjustment plate 51. Accordingly, the penis can be supported only by the wearing unit 50 and the decompression unit 30 without using the longitudinal support member 20.

The belt 52 wraps the shoulders on the back of the user and extends to the breast in such a way that both ends thereof are connected to each other on the breast. In detail, as shown in FIG. 14, on the front portion of the user, the belt 522 which is put on the breast of the user around the neck extends to the back of the user and goes below the shoulders (see reference numerals 523 and 524) before both ends thereof are connected to each other on the breast (see reference numeral 521). Of course the belt 52 may be put on the user by winding it around the neck and the chest of the user, but it is also possible that it is wound around only either of the neck or the chest. Reference numerals 521, 522, 523 and 524 shown in FIGS. 14 and 15 only designates several portions of the single belt 52 that correspond to body portions of the user around which it wound, rather than indicating different belts.

The first fastener 53 comprises a catch and a hook which are respectively provided on both ends of the belt 521 so that the belt 521 wound the chest of the user is fastened to the chest by locking the hook to the catch. The locked state of the first fastener 53 can be easily released by pressing opposite sides of the hook.

Furthermore, in the present invention, although the hook type fastener is illustrated as one example, a velcro tape, a zipper or a button type fastener may be used.

The buckles 54 is movably provided around the respective opposite portions of the belt 52 that are wound around the shoulders and extend onto the back of the user. The buckles 54 are connected to the horizontal buckle connection members 56 provided between the vertical opposite portions of the belt 52 and can be moved along the belt 52 upwards or downwards so that the distance between the opposite portions of the belt 52 can be adjusted depending on the length and width of the upper body of the user.

The buckle connection members 56 are horizontally oriented and connected to the corresponding buckles 54 that are provided on the opposite portions of the belt 52 that are wound around the shoulders. The adjacent ends of the buckle connection members 56 are fastened to the second fastener 55. In other words, the buckle connection members 56 extend inwards from the corresponding buckles 54 provided on the opposite portions of the belt 52 that are wound around the shoulders. The second fastener 55 is coupled to the facing inner ends of the buckle connection members 56. Thus, the distance between the opposite portions of the belt 52 can be appropriately adjusted depending on the length and width of the upper body of the user both by adjusting the length of the buckle connection members 56 and by moving them along the belt 52 upwards or downwards.

The second fastener 55 comprises a catch and a hook, which are respectively provided on the corresponding ends of the buckle connection members 56, so that the buckle connection members 56 are fastened to each other by locking the hook to the catch. In the same manner the second fastener 55 can also be embodied by various structures, such as a velcro tape, a button, a zipper, etc. as well as the above-mentioned fastening structure.

The operation and effect of the traction apparatus of the present invention having the above-mentioned construction will be described below.

The technical spirit of the present invention is characterized in that the decompression unit 30 can be supported only by the wearing unit 50 or it can be put on the user only by the longitudinal support members 20 without using the wearing unit 50. However, in this embodiment, for detailed explanation of the present invention, traction of the penis shaft 1 and the glans 2 using the wearing unit 50, the decompression unit 30 and the longitudinal support members 20 together will be explained.

First the user adjusts a shoulder width of the belt by adjusting the second fastener 55 and the buckles 54 and puts on the belt in such a way that the belt is wound around the shoulders and the chest. Thereafter, the user tightens the belt to fit the belt to his body size before locking the first fastener 53.

Subsequently, the user inserts his penis between the curved part 14 and the support protrusion 11 and adjusts the lengths of the longitudinal support members 20 so that the glans can be inserted into the decompression body 31. Here the length of each longitudinal support member 20 may be adjusted by adjusting the coupling position between the insert rod 22 and the receiving rod 23 using the insert fastening unit 25 or, alternatively, not only by adjusting the coupling position between the insert rod 22 and the receiving rod 23 but also selectively by rotating the threaded extension rod 212 forward or reverse using the rotational knob 211 to adjust the length of the base coupling rod 21.

Preferably, the user applies a lubricant, such as oil, lotion or the like, to the glans 2. The user thereafter inserts the penis into the base member 10, particularly, through the support protrusion 11 or the curved part 14, and then brings the base member 10 into contact with the root portion of the penis in such a way that it is oriented in the horizontal direction.

Subsequently, the user holds the decompression unit 30 with one hand, for example, the left hand, and pushes it to the penis such that the springs 321 of the support rods 32 are contracted and the penis comes into contact with the opening of the decompression body 31. The user thereafter connects an air suction pump (not shown) to the air suction valve 35 using his right hand.

After the glans 2 has been brought into contact with the decompression body 31, the user operates the air suction pump to suction out air from the decompression body 31, thus creating a vacuum in the decompression body 31. Then, the glans 2 is received into the decompression body 31 and inflated by vacuum pressure. After the air suction pump has been removed, the vacuum state is maintained and the springs 321 of the support rods 32 hold the penis.

Thereafter, the user orients in the vertical direction the decompression unit 30 holding the glans 2 and the longitudinal support members supporting the decompression unit 30, and locks the elastic connection member 41 to a selected appropriate one of the locking holes 511 of the height adjustment plate 51 of the wearing unit 50 which is put on the user, thus completing the wearing of the traction apparatus.

After the user has worn the fraction apparatus, even if the penis erects or the traction apparatus is shaken by a shock applied thereto, the fraction apparatus can be stably maintained, because the receiving rods 23 are movable in the longitudinal direction by the elastic force of the springs 321 of the support rods 32. Therefore, the traction apparatus can be reliably used regardless of surroundings or environment of the user. Furthermore, the base member 10 has an elliptical shape which is partially open so that even when the user sits down and stands up, the base member 10 is prevented from coming into contact with the testes and thus does not restricts the movement of the user.

To release the penis that has been under the traction force, the user opens the air suction valve 35 to release the vacuum state of the decompression body 31 and then removes the glans 2 from the decompression body 31. At this time, along with the glans 2, the elastic folded part 34 which has been folded state is drawn out of the decompression body 31, so that the glans 2 can be easily removed from the decompression body 31 without getting injured despite both the diameter of the opening of the decompression body 31 which is less than that of the glans 2 and the rigidity of the opening rim 311. Thereafter, the user removes the connection wire 42 from the body connector 33, loosens the first fastener 53, and then takes off the wearing unit 50, thus completing the removal of the traction apparatus.

Furthermore, in the present invention, as stated above, traction of the penis can be embodied only by the wearing unit 50, the decompression unit 30 and the connection unit 40 without using the longitudinal support member 20. In brief, the length of the belt 52 is adjusted by adjusting the first fastener 53 and the second fastener 55 to correspond it to the body size of the user before the user puts on the wearing unit 50. Thereafter, the user applies oil or lotion to the glans 2 of the penis, holds the decompression body 31, for example, with his left hand, and inserts the glans 2 into the decompression body 31.

After the glans 2 has been inserted into the decompression body 31, the user connects the air suction device to the air suction valve 35 and creates a vacuum in the decompression body 31 to inflate the glans 2.

After the glans 2 has been held by the decompression body 31, the user appropriately adjusts the height at which the elastic connection member 41 is locked to the height adjustment plate 51 of the wearing unit 50 so that the effect of extending the penis is obtained. In other words, in the present invention, the function in which the penis is extended by extending the length of the longitudinal support member 20 and a curvature phenomenon of the penis, for example, penis plastica, is treated thereby can also be realized by adjusting the height at which the elastic connection member 41 is locked to the height adjustment plate 51 in place of using the longitudinal support member 20.

Furthermore, the glans 2 which is inserted into the decompression body 31 is inflated by suction pressure in the decompression body and is caught by the opening rim 311 at the portion between the glans 2 and the penis shaft 1. Thus, the glans 2 is prevented from being undesirably removed from the decompression body 31. In addition, the glans 2 is elastically supported by the elastic folded part 34 so that it is prevented from getting injured. Therefore, in the present invention, supporting the decompression body 31 by the wearing unit 50 is reliably accomplished. As mentioned above, likewise, traction of the penis can, of course, be realized only by the longitudinal support members 20, the decompression unit 30 and the base member 10 without using the wearing unit 50.

Figure 16:
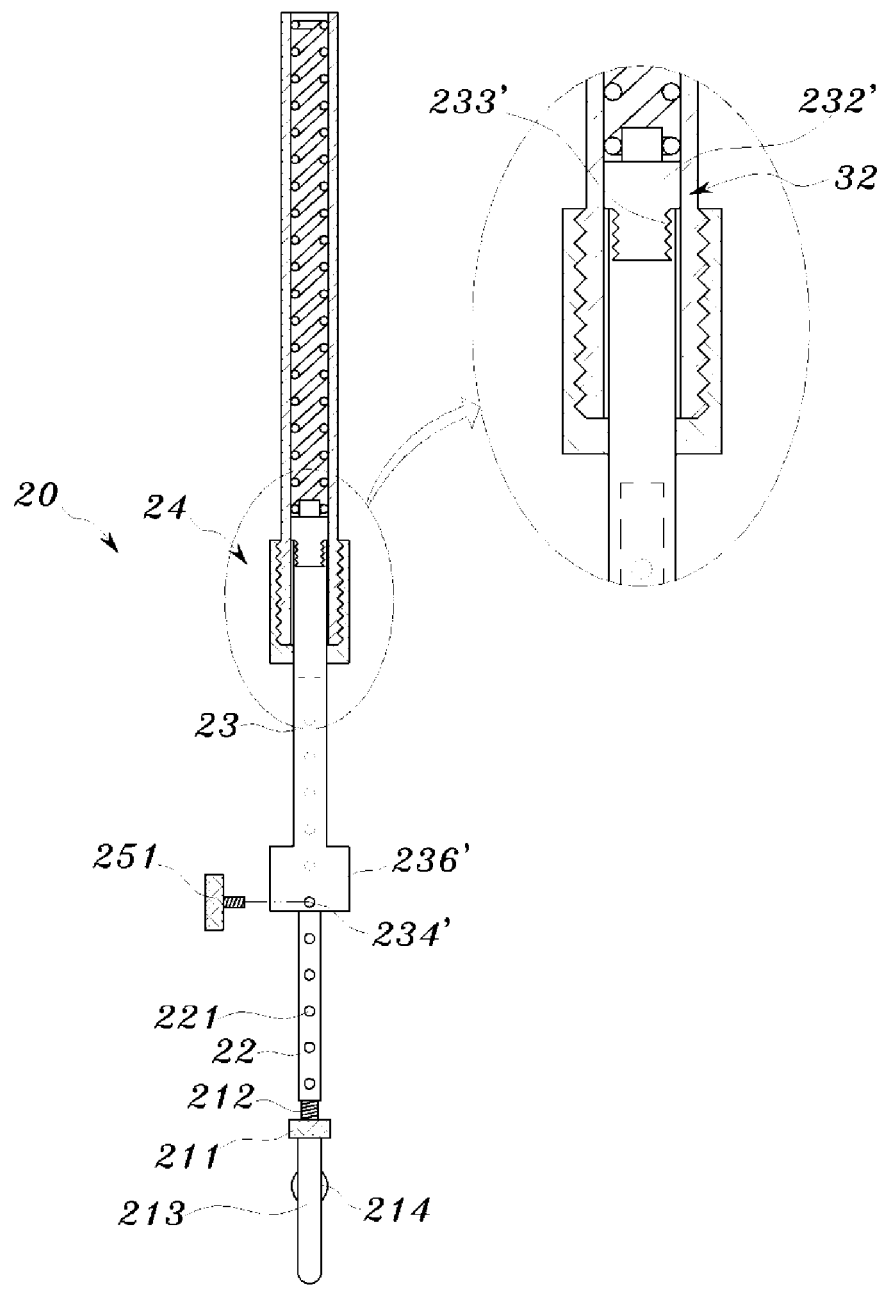
FIG. 16 is a view showing another embodiment of a receiving rod as another embodiment of the fraction apparatus according to the present invention.

FIG. 16 is a view showing another embodiment of the receiving rod as another embodiment of the fraction apparatus according to the present invention.

Referring to FIG. 16, a receiving rod 23 of the fraction apparatus according to the present invention may be configured as another embodiment, as shown in the following description. In this embodiment, the receiving rod 23 includes a first end 236', a screw fastening hole 234' and an end stopper 232'. The first end 236' is integrally provided with the insert fastening unit 25. The insert rod 22 is inserted into the first end 236'. The screw fastening hole 234' is formed through a circumferential outer surface of the first end 236' so that the fastening screw 251 is inserted into the screw fastening hole 234'. The end stopper 232' is threaded into a second end of the receiving rod 23 that is inserted into the support rod 32. The first end 236' of the receiving rod 23 has slide grooves 253 on the inner surface thereof, in the same manner as that of the prior embodiment.

In this embodiment, because the first end 236' of the receiving rod 23 is integrally provided with the insert fastening unit 25, the slide groove (253, refer to FIGS. 11 and 12) into which the corresponding stop protrusions 222 of the insert rod 22 are slidably inserted are formed in the inner surface of the first end 236'. In addition, the screw fastening hole 234' is formed through the outer surface of the first end 236' so that the fastening screw 251 is tightened into a selected one of the fastening holes 221 of the insert rod 22 via the screw fastening hole 234'.

The end stopper 232' which is provided on the second end of the receiving rod 23 is inserted into the support rod 32 and is brought into close contact with the rear end of the spring 321. The end stopper 232' has an external thread on a rear end thereof so that the external thread engages with an internal thread 233' formed in the inner surface of the second end of the receiving rod 23.

In other words, this embodiment of the present invention is configured in such a way that the receiving rod 23 can be separated from the coupling unit 24 by thread rotating the receiving rod 23 with respect to the end stopper 232'. Thus, the removal of the receiving rod 23 from the coupling unit 24 can be facilitated. In addition, because the receiving rod 23 is integrally provided with the insert fastening unit 25, the number of components of the traction apparatus is reduced, and the assembly and disassembly process can be simplified.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A traction apparatus for a penis, comprising:
a decompression unit adapted to receive a glans of the penis therein and to inflate the glans; a wearing unit comprising a belt to be wound around an upper body of a user, and a height adjustment plate connected to the belt, the height adjustment plate extending a predetermined length in a vertical direction in such a way that a height of the decompression unit is adjustable; and
a connection unit coupled to the decompression unit and to the height adjustment plate so that the decompression unit is connected to the wearing unit by the connection unit.

2. A traction apparatus for a penis, comprising:
a base member having a predetermined shape to receive the penis inserted into the base member, the base member supporting a lower portion of the penis inserted thereinto;
longitudinal support members coupled at first ends thereof to a base member, each of the longitudinal support members being adjustable in length; and
a decompression unit adapted to receive a glans of the penis therein and to inflate the glans, the decompression unit being coupled to second ends of the longitudinal support members so that the decompression unit is supported by the longitudinal support members.

3. A traction apparatus for a penis, comprising:
a base member having a predetermined shape to receive the penis inserted into the base member, the base member supporting a lower portion of the penis inserted thereinto;
longitudinal support members coupled at first ends thereof to a base member, each of the longitudinal support members being adjustable in length;
a decompression unit adapted to receive a glans of the penis therein and to inflate the glans, the decompression unit being coupled to second ends of the longitudinal support members so that the decompression unit is supported by the longitudinal support members;
a wearing unit comprising a belt to be wound around an upper body of a user, and a height adjustment plate connected to the belt, the height adjustment plate extending a predetermined length in a vertical direction in such a way that a height of the decompression unit is adjustable; and
a connection unit coupled to the decompression unit and to the height adjustment plate so that the decompression unit is connected to the wearing unit by the connection unit.

4. The traction apparatus as set forth in claim 1, further comprising:
a base member; and
longitudinal support members coupled at first ends thereof to the base member and at second ends to the decompression unit.

5. The traction apparatus as set forth in any one of claims 2 through 3 and 4, wherein the decompression unit comprises:
a decompression body adapted to receive the glans of the penis therein;
an elastic folded part made of an elastic material and provided around an opening of the decompression body in such a way that the elastic folded part is folded between an inside and an outside of the decompression body, the elastic folded part elastically supporting the inserted penis;
support rods extending in a longitudinal direction, each of the support rods having a first end into which the corresponding longitudinal support member inserted, with a spring provided in each of the support rods so that the support rod elastically supports the corresponding longitudinal support member;

a body connector extending to opposite sides from the decompression body so that the decompression body is coupled to the support rods by the body connector; and an air suction valve for sucking out air from the decompression body.

6. The traction apparatus as set forth in claim 5, wherein the body connector is integrated with the decompression body and has in each of opposite side edges thereof an insert slot into which the corresponding support rod is fitted, and an insert flange protrudes from an outer surface of each of the support rods and is removably fitted into the corresponding insert slot of the body connector.

7. The traction apparatus as set forth in claim 2 or 3, wherein the base member comprises:

a curved part having a curved shape and supporting an outer surface of the penis;

support protrusions extending from opposite sides of the curved part in such a way that distal ends thereof face each other;

coupling protrusions protruding forwards from the base member between the curved part and the support protrusion, with a coupling hole formed in each of the coupling protrusion so that the first end of the corresponding longitudinal support member is inserted into the coupling hole; and an upper protruding support protruding forwards from an upper portion of the curved part, the upper protruding support supporting the inserted penis.

8. The traction apparatus as set forth in claim 2 or 3, wherein each of the longitudinal support members comprises:

a base coupling rod having a first end inserted into the base member, and a second end extending in the longitudinal direction;

an insert rod into which the second end of the base coupling rod is inserted in such a way that the base coupling rod is movably coupled to the insert rod, with at least one fastening hole formed through an outer surface of the insert rod; and a receiving rod having a first end into which the insert rod is inserted in such a way that the insert rod is coupled to the receiving rod so as to be adjustable in a length of combination of the insert rod and the receiving rod, and a second end inserted into the decompression unit.

9. The traction apparatus as set forth in claim 8, wherein the base coupling rod comprises:

a base insert rod inserted at a first end thereof into the base member, with a locking protrusion provided on an outer surface of the base insert rod;

a threaded extension rod extending from a second end of the base insert rod, with an external thread formed on an outer surface of the threaded extension rod so that the threaded extension rod is thread coupled to the insert rod; and a rotational knob fastened around a circumferential outer surface of the threaded extension rod so that a length to which the base coupling rod is extracted from the insert rod 1 is adjusted by rotating the rotational knob.

10. The traction apparatus as set forth in claim 8, wherein the longitudinal support member further comprises: a coupling unit having a hole formed through the coupling unit in a longitudinal direction thereof so that the receiving rod is movably inserted into the hold of the coupling unit, with an internal thread formed on a circumferential inner surface of the coupling unit, and a stop ring protruding inwards from the circumferential inner surface of the coupling unit, and the receiving rod comprises: an end stopper thread-coupled to the second end of the receiving rod, the end stopper having a diameter greater than an inner diameter of the stop ring of the coupling unit so that the end stopper is stopped by the stop ring; and an external threaded ring provided on a circumferential outer surface of the first end of the receiving rod into which the insert rod is inserted, with a fastening ring threaded over the external threaded ring.

11. The traction apparatus as set forth in claim 8, wherein the longitudinal support member further comprises:

an insert fastening unit coupled to the fastening hole via a circumferential outer surface of the receiving rod so that the insert rod is fastened to the receiving rod, the insert fastening unit comprising: a fastening ring fastened to the circumferential outer surface of the receiving rod; and a fastening screw threaded into the fastening hole of the insert rod via the fastening ring so that the insert rod is fastened to the receiving rod.

12. The traction apparatus as set forth in claim 1 or 3, wherein the connection unit comprises:

a connection wire fastened to the decompression unit; and an elastic connection member connected to the connection wire and the wearing unit to provide an elastic restoring force.

13. The traction apparatus as set forth in claim 1 or 3, wherein the height adjustment plate has a plurality of locking holes arranged in a longitudinal direction of the height adjustment plate, and the connection unit is selectively locked to one of the locking holes so that a height at which the connection unit is locked to the height adjustment plate is adjusted.

14. A traction apparatus for a penis, comprising:

a base member having a predetermined shape to receive the penis inserted into the base member, the base member supporting a lower portion of the penis inserted thereinto;

longitudinal support members coupled at first ends thereof to a base member, each of the longitudinal support members being adjustable in length; and a decompression unit adapted to receive a glans of the penis therein and to inflate the glans, the decompression unit being coupled to second ends of the longitudinal support members so that the decompression unit is supported by the longitudinal support members, and having a decompression body adapted to receive the glans of the penis therein;

an elastic folded part made of an elastic material and provided around an opening of the decompression body in such a way that the elastic folded part is folded between an inside and an outside portion of the decompression body, the elastic folded part elastically supporting the penis inserted therein; and an air suction valve for sucking out air from the decompression body.

* * * * *